US006408048B2

(12) United States Patent
Opsal et al.

(10) Patent No.: US 6,408,048 B2
(45) Date of Patent: Jun. 18, 2002

(54) APPARATUS FOR ANALYZING SAMPLES USING COMBINED THERMAL WAVE AND X-RAY REFLECTANCE MEASUREMENTS

(75) Inventors: Jon Opsal, Livermore; Allan Rosencwaig, Danville, both of CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 09/761,132

(22) Filed: Jan. 16, 2001

Related U.S. Application Data (60) Provisional application No. 60/189,334, filed on Mar. 14, 2000.

(51) Int. Cl.[7] .......................... G01B 15/02; G01N 21/47
(52) U.S. Cl. .............................. 378/89; 378/76; 378/70; 356/432
(58) Field of Search ................. 378/86, 88, 89, 378/90, 76; 356/432

(56) References Cited

U.S. PATENT DOCUMENTS

| | | | |
|---|---|---|---|
| 4,521,118 A | 6/1985 | Rosencwaig | 374/5 |
| 4,634,290 A | 1/1987 | Rosencwaig et al. | 374/5 |
| 4,636,088 A | 1/1987 | Rosencwaig et al. | 374/5 |
| 4,821,302 A * | 4/1989 | Whitlock et al. | 378/73 |
| 4,854,710 A | 8/1989 | Opsal et al. | 356/432 |
| 4,952,063 A * | 8/1990 | Opsal et al. | 356/432 |
| 4,999,014 A | 3/1991 | Gold et al. | 356/382 |
| 5,042,952 A * | 8/1991 | Opsal et al. | 356/432 |
| 5,074,669 A | 12/1991 | Opsal | 356/445 |
| 5,181,080 A | 1/1993 | Fanton et al. | 356/381 |
| 5,228,776 A | 7/1993 | Smith et al. | 374/5 |
| 5,249,216 A * | 9/1993 | Ohsugi et al. | 378/46 |
| 5,619,548 A | 4/1997 | Koppel | 378/70 |
| 5,798,837 A | 8/1998 | Aspnes et al. | 356/369 |
| 5,877,859 A | 3/1999 | Aspnes et al. | 356/364 |
| 5,978,074 A | 11/1999 | Opsal et al. | 356/72 |
| 6,005,915 A * | 12/1999 | Hossain et al. | 378/86 |
| 6,108,087 A | 8/2000 | Nikoonahad et al. | 356/359 |

FOREIGN PATENT DOCUMENTS

WO    WO 99/02970    1/1999    .......... G01N/21/21

OTHER PUBLICATIONS

T. Boudet et al., "Optical and x-ray characterization applied to multilayer reverse engineering," *Opt. Eng.*, vol. 37, No. 7, Jul. 1998, pp. 2175–2181.

P. Boher et al., "A new versatile system for characterization of antireflective coatings using combined spectroscopic ellipsometry and grazing x-ray reflectance," (part of the EUROPTO Conference of Lithography for Semiconductor Manufacturing, Edinburgh, Scotland) *SPIE*, vol. 3741, May 1999, pp. 104–114.

L.G. Parratt, "Surface Studies of Solids by Total Reflection of X-Rays," *Physical Review*, vol. 95, No. 2, Jul. 15, 1954, pp. 359–369.

(List continued on next page.)

*Primary Examiner*—Robert H. Kim
*Assistant Examiner*—Allen C Ho
(74) *Attorney, Agent, or Firm*—Stallman & Pollock LLP (57) ABSTRACT

This invention provides a measurement device that includes both an X-ray reflectometer and a thermal or plasma wave measurement module for determining the characteristics of a sample. Preferably, these two measurement modules are combined into a unitary apparatus and arranged to be able to take measurements at the same location on the wafer. A processor will receive data from both modules and combine that data to resolve ambiguities about the characteristics of the sample. The processor can be part of the device or separate therefrom as long as the measurement data is transferred to the processor.

18 Claims, 3 Drawing Sheets

OTHER PUBLICATIONS

M.F. Toney, "Measurements of carbon thin films using x–ray reflectivity," *J. Appl. Phys.*, vol. 66, No. 4, Aug. 15, 1989, pp. 1861–1863.

J.T. Fanton et al., "Multiparameter measurements of thin films using beam–profile reflectometry," *J. Appl. Phys.*, vol. 73, No. 11, Jun. 1, 1993, pp. 7035–7040.

J.M. Leng et al., "Simultaneous measurement of six layers in a silicon on insulator film stack using spectrophotometry and beam profile reflectometry," *J. Appl. Phys.*, vol. 81, No. 8, Apr. 15, 1997, pp. 3570–3578.

U.S. application No. 09/629,407, filed Aug. 1, 2000, entitled: "Measurement of Thin Films and Barrier Layers on Patterned Wafers with X–Ray Reflectometry," pp. 1–23 (including 5 sheets of drawings).

U.S. application No. 09/527,389, filed Mar. 16, 2000, entitled: "Calibration and Alignment of X–Ray Reflectometric Systems," pp. 1–33 (including 14 sheets of drawings).

* cited by examiner

APPARATUS FOR ANALYZING SAMPLES USING COMBINED THERMAL WAVE AND X-RAY REFLECTANCE MEASUREMENTS

PRIORITY

This application claims the benefit of U.S. Provisional Application No. 60/189,334, which provisional application was filed on Mar. 14, 2000 and is hereby incorporated by reference in its entirety.

FIELD OF THE INVENTION

The present invention relates to the field of metrology tools for measuring semiconductor wafers and, in particular, relates to a tool that combines two complementary types of measurements into a single tool to reduce ambiguities in both types of measurements.

BACKGROUND OF THE INVENTION

The semiconductor industry has a continuing interest in measuring various thin film layers formed on semiconductor wafers. A number of metrology devices have been developed for making these measurements.

One example of such an apparatus is disclosed in PCT application WO/9902970, published Jan. 21, 1999. The assignee herein has commercialized the device described in that patent application under the name OPTI-PROBE 5240. This device includes a number of measurement technologies. More specifically, the device includes a beam profile ellipsometer (BPE) (see U.S. Pat. No. 5,181,080); a beam profile reflectometer (BPR) (see U.S. Pat. No. 4,999,014); relatively conventional broad band (BB) and deep ultraviolet (DUV) spectrometers; a proprietary broad band spectroscopic ellipsometer (SE) (see U.S. Pat. No. 5,877,859) and an off-axis narrow band ellipsometer (see U.S. Pat. No. 5,798,837). All of the above-recited patents and PCT applications are incorporated herein by reference.

The above described system is particularly suited for characterizing relatively transparent films, such as silicon dioxide, on semiconductors. This measurement system is somewhat less useful when analyzing opaque films such as metals.

An optical technique which is particularly suited for measuring the thickness of very thin, metal films is X-ray reflectometry. Using a probe beam generated by a source of very short wavelength radiation, thin films can be analyzed which are opaque to both visible and UV wavelengths. One example of such a system is described in U.S. Pat. No. 5,619,548, issued Apr. 8, 1997, and incorporated herein by reference.

In an X-ray reflectometer, a probe beam of X-ray radiation is directed to impinge on the sample at an angle so that it is at least partially reflected. A sample may typically consist of a substrate covered by one or more thin metal layers. At very shallow angles, below a critical angle ($\Psi_c$) (as measured between the surface of the sample and the incoming ray), all of the X-ray radiation will be reflected. Typical incidence angles are very shallow, near grazing incidence, because the reflectivity falls very quickly as the angle is increased above the critical angle. As the angle of incidence of the incoming beam increases, an increasing amount of radiation will be transmitted through the top metal layer and the amount of reflected light will be reduced. Some of the radiation transmitted through the metal layer(s) will reach the interface between the metal film and the substrate and be reflected from the substrate. The radiation reflected at the interfaces among the metal film layers and the substrate will interfere, giving rise to a reflectivity curve showing interference effects. By analyzing the dependence of the reflectivity on the angle of incidence, one can independently determine both the thickness and density of the thin film layers on the sample.

The added capability offered by an X-ray reflectometer has led prior researchers to attempt to combine the measurements from an X-ray reflectometer with those of other optical measurement tools. For example, samples have been analyzed using a combination of grazing X-ray reflectometry and spectroscopic ellipsometry. (See, "*A new versatile system for characterization of antireflective coatings using combined spectroscopic ellipsometry and grazing X-ray reflectance,*" Boher, SPIE, Vol. 3741, page 104, May 1999.) Other researchers have proposed combining X-ray refletdometry with infrared spectroscopy and transmission spectroscopy. In addition, researchers have also discussed the desirability of obtaining multiple separate measurements including X-ray reflectometry, variable angle of incidence reflectometry and "mirage" style, photo-thermal measurements to evaluate a sample. (See, "*Optical and X-ray characterization applied to multilayer reverse engineering,*" Boudet, Optical Engineering, Vol. 37 (1), page 2175, July 1998). In this paper, the authors used the photothermal method to analyze losses from absorption.

The inventors herein have recognized that there are further advantages to combining the measurements that can be obtained from X-ray reflectometry with measurements that can be obtained from a thermal and/or plasma wave analysis. A thermal and plasma wave metrology device is marketed by the assignee herein under the name of Therma-Probe. This device incorporates technology described in the following U.S. Pat. Nos. 4,634,290; 4,346,088; 4,854,710 and 5,074,669. The latter patents are incorporated herein by reference.

In the basic device described in the patents, an intensity modulated pump laser beam is focused on the sample surface for periodically exciting the sample. In the case of a metal, thermal waves are generated, while in a semiconductor, both thermal and plasma waves are generated. These waves spread out from the pump beam spot and reflect and scatter off various features and interact with various regions within the sample in a way which alters the flow of heat and/or plasma from the pump beam spot.

The presence of the thermal and plasma waves has a direct effect on the reflectivity at the surface of the sample. Features and regions below the sample surface which alter the passage of the thermal and plasma waves will therefore alter the optical reflective patterns at the surface of the sample. By monitoring the changes in magnitude and/or phase of the reflectivity of the sample at the surface, information about characteristics below the surface can be investigated.

In the basic device, a second laser is provided for generating a probe beam of radiation. This probe beam is focused colinearly with the pump beam and reflects off the sample. A photodetector is provided for monitoring the periodic changes in the magnitude and phase of the reflected probe beam. The photodetector generates an output signal which is proportional to the reflected power of the probe beam and is therefore indicative of the varying optical reflectivity of the sample surface.

The output signal from the photodetector is filtered to isolate the changes which are synchronous with the pump beam modulation frequency. In the preferred embodiment, a lock-in detector is used to monitor the magnitude and phase of the periodic reflectivity signal. This output signal is conventionally referred to as the modulated optical reflectivity (MOR) of the sample.

This system has been used successfully to measure ion implantation levels in semiconductors. Such a system can also be used to measure thermal conductivity or thermal diffusion in a thin film layer on a sample (see U.S. Pat. No. 5,074,669, incorporated by reference). Such a system can also be used to measure characteristics of thin metalized layers (see U.S. Pat. No. 5,978,074, incorporated by reference).

Other techniques besides modulated optical reflectivity detection can be used to monitor the effects of thermal and plasma wave propagation in a sample. For example, various interferometry and mirage effects techniques have been used. The broad scope of the subject invention includes these techniques as well. (See for example, U.S. Pat. No. 6,108,087).

Since an X-ray, reflectometer measurement permits determination of both thickness and density independently, it has been recognized by the inventors herein that special benefits can be obtained by analyzing a sample using a combination of X-ray reflectometry along with a thermal and plasma wave measurement technique. More specifically, if information about the thickness and/or density of the thin film can be obtained using an X-ray reflectometer measurement, the remaining variables (such as the index of refraction and thermal conductivity) can be more easily determined with a thermal wave tool since one less variable needs to be resolved through the analysis of the data.

SUMMARY OF THE INVENTION

Accordingly it is an object of this invention to provide a measurement device that includes both an X-ray reflectometer and a thermal and plasma wave measurement module for determining the characteristics of a sample. Preferably, these two measurement modules are combined into a unitary apparatus and arranged to be able to take measurements at the same location on the wafer. A processor will receive data from both modules and combine that data to resolve ambiguities about the characteristics of the sample. The processor can either be part of the unitary apparatus or separate therefrom as long as the measurement data is transferred to the processor. In either case, the apparatus is unitary so long as the X-ray reflectometer and the thermal and/or plasma wave measurement modules are combined into a single device.

DETAILED DESCRIPTION OF THE INVENTION

The subject combination can be used effectively on samples with complex multilayer samples. For example, consider a silicon wafer upon which has been deposited a thin layer of tantalum nitride (250 Angstroms) covered by a relatively thicker layer of copper (2000 Angstroms or greater). Tantalum nitride is a relatively opaque metallic material. For such a sample, an X-ray reflectometer measurement would be able to accurately determine the thickness of the thin intermediate layer of tantalum nitride. This is so because the X-rays will penetrate the copper and reflect off the tantalum nitride. The interference fringes can then be analyzed to determine layer thicknesses. In addition, the X-ray reflectance measurements can also provide information about the density of the top copper layer. However, the X-ray reflectance measurements can less easily determine the thickness of the copper layer since any interference fringes associated with that layer would be too closely spaced together to allow resolution. Nonetheless, the thickness of the thicker copper layer can easily be measured using a thermal wave analysis. The tantalum nitride layer will essentially be invisible to the thermal wave analysis. By combining the two measurements in a single tool, the user can more readily obtain a greater amount of information about the multilayer structure.

In addition, thermal wave measurements can also be used to determine the diffusivity of a layer. Diffusivity is a function of the thermal conductivity, density, and the specific heat of the material. For most materials, the specific heat does not vary significantly within a given layer. As noted above, X-ray reflectometry can be used to determine the density of a layer. Thus, by combining X-ray reflectometry measurements (which enable a density analysis) with thermal wave measurements (which enable a diffusivity analysis), the thermal conductivity of the layer can be determined even if the thickness of the layer is unknown. It is also possible to evaluate sheet resistance based on the calculated thermal conductivity of the material.

Another advantage of the subject combination relates to product wafer measurement capability. It is known that the assignee's Therma-Probe system can measure on product wafers with small feature sizes. In part this capability arises from the smallness of the focused pump and probe beam spot size on the sample in conjunction with accurate wafer positioning controls. While the X-ray reflectometry spot tends to be significantly larger than the thermal wave test spot, it has been shown by the assignee herein that the X-ray interaction can also be used on product wafers. This relationship is described in co-pending application Ser. No. 09/629,407, filed Aug. 1, 2000, and incorporated herein by reference. In brief, it has been found that the X-rays do not scatter very strongly when interacting with structures found on product wafers. Therefore, using a proper analysis an X-ray reflectometer can characterize blanket film structures deposited on a product wafer almost as easily as if the wafer were a test wafer. Since both of these technologies can provide information about product wafers, the combination can be used to further analyze structures on product wafers thereby minimizing the need for test wafers.

Providing multiple measurement tools in a single device has added benefits. For example, it is possible to arrange the optical systems to measure on the same point on the wafer without moving the wafer. In addition, a single tool has a smaller footprint and therefore takes up less floor space in the semiconductor fabrication facility. By combining technologies in a single tool, costs can be reduced by eliminating duplicate subsystems such as wafer handlers and computers. Finally, the combination can simplify and streamline decision making since the information from the two measurement modalities can be coordinated instead of producing conflicting results as in the prior art when two separate devices might be used.

Further analytical capability can be obtained if the device is arranged to include additional measurement modalities. Such additional measurement modalities can include one or more optical metrology devices of the type found in the assignee's OPTI-PROBE 5240, discussed above.

Figure 1:
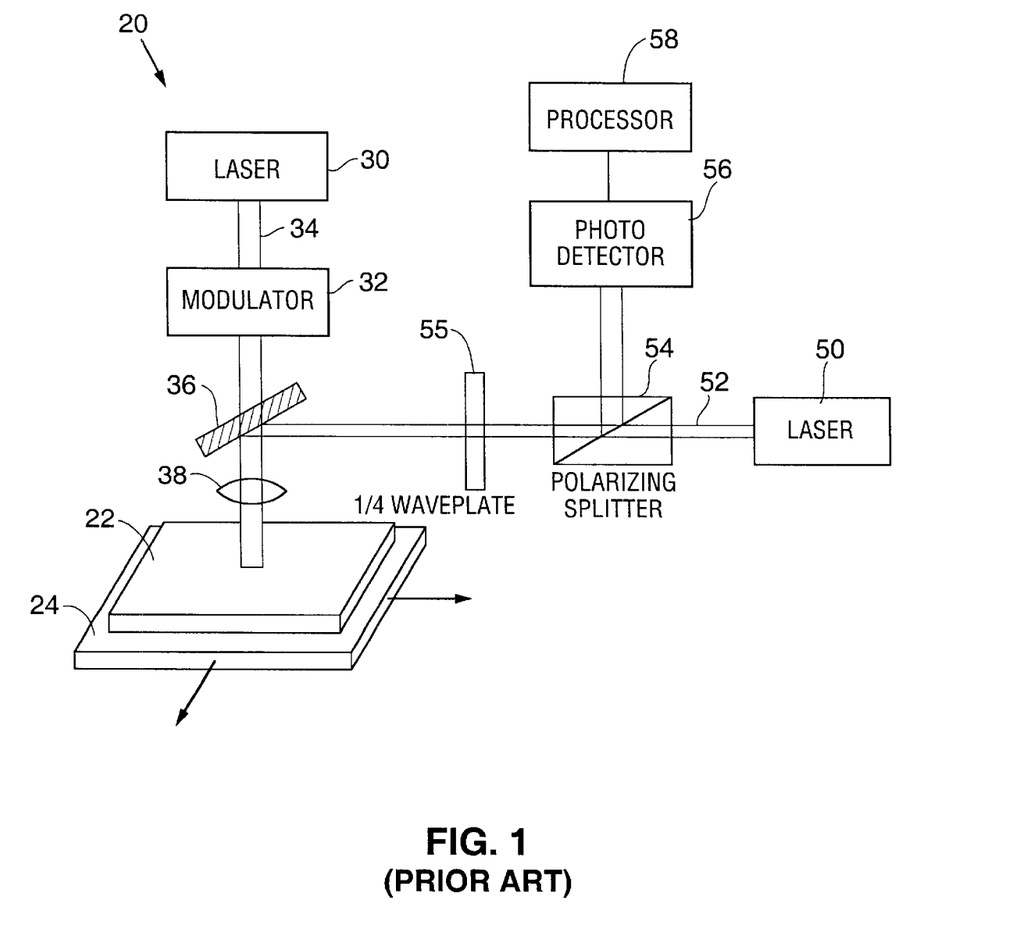
FIG. 1 is a composite block and schematic diagram of an apparatus for carrying out the detection of thermal and plasma waves in accordance with the subject invention.

Referring to FIG. 1, there is illustrated an apparatus 20 for monitoring thermal and plasma waves. The apparatus of FIG. 1 illustrates only the basic elements. Those skilled in the art will understand that a commercial devices will be more complex. More details of a thermal wave system are disclosed in U.S. Pat. No. 5,978,074, cited above.

As seen in FIG. 1, a sample 22 rests on a platform 24. Platform 24 is capable of movement in two orthogonal directions in a manner such that the sample can be rastered with respect to the heating and probe beams of the subject invention.

The means for generating thermal and plasma waves includes a laser 30 emitting a beam 34 which is intensity modulated by modulator 32. In the preferred embodiment, beam 34 is focused on the surface of the sample by a microscopic objective 38. Beam 34 is intended to periodically excite the, sample surface. This periodic excitation is the source of thermal and plasma waves that propagate outwardly from the center of the beam. The plasma and thermal waves interact with sample boundaries and barriers in a manner that is mathematically equivalent to scattering and reflection of conventional propagating waves. Any features on or beneath the surface of the sample that have thermal or plasma diffusion characteristics different from their surroundings will reflect and scatter thermal and plasma waves and thus become visible to these waves.

The detection system includes a laser 50 for emitting a probe beam 52. Probe beam 52 is directed onto a region of the sample surface that has been periodically heated by the modulated energy beam 34. Probe beam 52 is first passed through a polarizing splitter 54 oriented in a manner such as to let the coherent light emanating from laser 50 to pass freely therethrough. The splitter will, however, deflect all light whose phase has been rotated through 90 degrees relative to beam 52. The reason for this arrangement will become apparent below.

Light probe beam 52 is then passed through a ¼λ-waveplate 55. Waveplate 55 functions to rotate the phase of the probe beam by 45 degrees. As can be appreciated, on the return path of the beam, the waveplate will rotate the phase of the beam another 45 degrees so that when it reaches splitter 54 the phase of the beam will have been rotated a total of 90 degrees from the incoming orientation. By this arrangement, the splitter 54 will deflect the retro-flected light beam up to detector 56.

After the probe beam 52 initially passes through waveplate 55, it is reflected downwardly by dichroic mirror 36. The dichroic mirror is selected to be transparent to the pump beam wavelength and reflective of the probe beam wavelength. In the preferred embodiment, the pump beam and the probe beam are aligned in such a manner that they are directed in a coincident manner down through lens 38 and focused at the same spot on the surface of the sample. By focusing the pump and probe beams at the same spot, the maximum signal output can be achieved.

The probe beam is reflected back up to the dichroic mirror where it is, in turn, reflected back along the incoming path and through the ¼λ-waveplate 55. As discussed above, waveplate 55 rotates the phase of the probe beam by another 45 degrees such that when the beam reaches splitter 54, its phase has been rotated 90 degrees with respect to the original beam. Accordingly, this splitter will deflect the retro-reflected probe beam upwardly towards detector 56.

Since intensity variations of a radiation beam are to be detected, a standard photodetector may be employed as a sensing mechanism. The intensity variations which are measured are then supplied as an output signal to a processor for deriving the data on the thermal and plasma waves based on the changing surface temperature conditions as indicated by the changing output signal.

The operation of processor 58 is dependent on the type of testing configuration which is utilized. In all cases, the processor is designed to evaluate the intensity changes of the incoming probe beam which are the result of the periodic reflectivity changes caused by the periodic heating on the sample. These periodic intensity changes are filtered to produce a signal which may be evaluated. Details of a suitable detector and processor arrangement are disclosed in U.S. Pat. No. 5,978,074. The latter patent also discloses how thermal waves can be detected by monitoring the periodic angular deflections of a probe beam. As noted above, other techniques are known for thermal wave measurements including the mirage technique and interferometric techniques. (See for example, the articles cited of record in U.S. Pat. No. 4,521,118)

Figure 2:
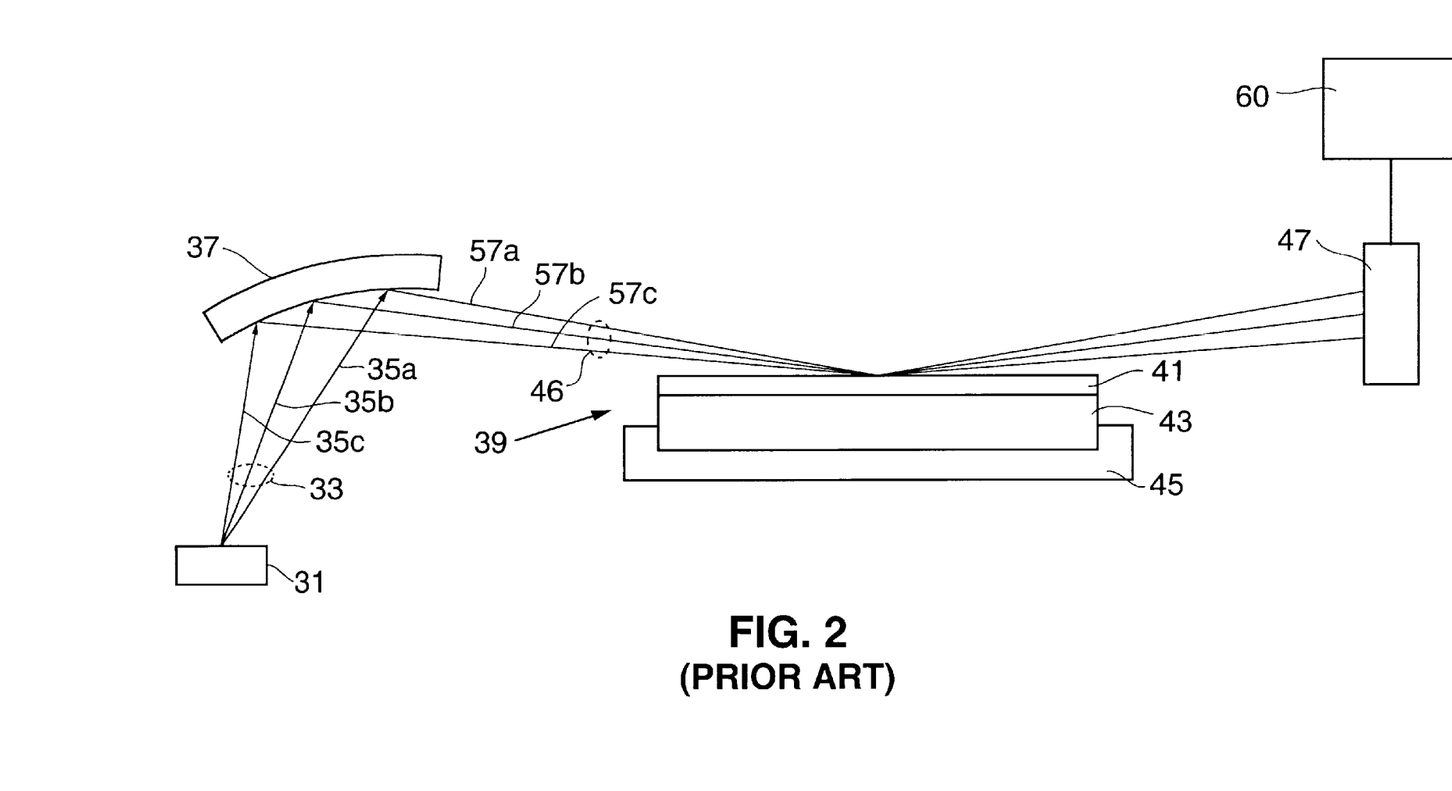
FIG. 2 is a composite block and schematic diagram of an apparatus for carrying out X-ray reflectometric measurements in accordance with the subject invention.

A preferred XRR technique for use in the subject combination is described in U.S. Pat. No. 5,619,548, issued Apr. 8, 1997, which is hereby incorporated by reference in its entirety. FIG. 2 illustrates the basic components for this technique. More details of a suitable XRR system can be found in U.S. Ser. No. 09/527,389, filed Mar. 16, 2000.

Referring to FIG. 2, the X-ray scattering system includes an X-ray source 31 producing an X-ray bundle 33 that comprises a plurality of X-rays shown as 35$a$, 35$b$, and 35$c$. An X-ray reflector 37 is placed in the path of the X-ray bundle 33. The reflector 37 directs the X-ray bundle 33 onto a test sample 39 held in a fixed position by a stage 45, and typically including a thin film layer 41 disposed on a substrate 43. Accordingly, a plurality of reflected X-rays, 57$a$, 57$b$, and 57$c$ (forming bundle 46) concurrently illuminate the thin film layer 41 of the test sample 39 at different angles of incidence. The X-ray reflector 37 is preferably a monochromator. The diffraction of the incident bundle of X-rays 33 within the single-crystal monochromator allows only a narrow band of the incident wavelength spectrum to reach the sample 39, such that the Bragg condition is satisfied for this narrow band. As a result, the plurality of X-rays 57$a$, 57$b$, and 57$c$, which are directed onto the test sample 39, are also monochromatic. A detector 47 is positioned to sense X-rays reflected from the test sample 39 and to produce signals corresponding to the intensities and angles of incidence of the sensed X-rays. A processor 60 is connected to the detector to receive signals produced by the detector in order to determine various properties of the structure of the thin film layer, including thickness, density and surface roughness.

In a basic system, a probe beam of X-ray radiation is directed to strike the sample at an angle selected so that it is at least partially reflected. A sample may typically consist of a substrate covered by one or more thin metal layers. At very shallow angles, below a critical angle ($\Psi_c$) (as measured between the surface of the sample and the incoming ray), all the X-ray radiation will be reflected. As the angle of incidence of the incoming beam increases with respect to the sample surface, an increasing amount of radiation will be transmitted through the top metal layer and the amount of reflected light will be reduced. Some of the radiation transmitted through the metal layer(s) will reach the interface between the metal film and the substrate and be reflected off the substrate.

The radiation reflected at the interfaces among the metal film layers and the substrate will interfere, giving rise to a reflectivity curve showing interference effects.

For a given sample of thin films, X-ray reflectivity can be determined using a Fresnel equation modeling as a function principally of X-ray wavelength ($\lambda$), angle of incidence, and the thicknesses and optical properties of the materials making up the layers. Typically the critical angle at which total reflection occurs is quite small (~0.1–0.5°). Because reflectivity falls very quickly as the angle of incidence is increased above the critical angle, small angle X-ray reflection is experimentally important. Under a small angle approximation ($\sin \psi \approx \psi$), a recursive formula for the X-ray reflectivity at an interface between a layer n-1 and a layer n is given by $$R_{n-1,n} = a_{n-1}^4 \left( \frac{R_{n,n+1} + F_{n-1,n}}{R_{n,n+1} F_{n-1,n} + 1} \right),$$

where $F_{n-1,n} = (f_{n-1} - f_n)/(f_{n-1} + f_n)$, and where $a_n = \exp((-i\pi/\lambda) f_n d_n)$.

Here $d_n$ is the thickness of layer n and $\psi_c(n)$ is the critical angle at which total reflection occurs for X-rays of wavelength $\lambda$ incident on material of layer n.

The $f_n$ are given by $f_n = A_n - iB_n$, where $A_n = (1/\sqrt{2})(\{[\psi^2 - \psi_c^2(n)]^2 + 4\beta_n^2\}^{1/2} + [\psi^2 - \psi_c^2(n)])^{1/2}$ $B_n = (1/\sqrt{2})(\{[\psi^2 - \psi_c^2(n)]^2 + 4\beta_n^2\}^{1/2} - [\psi^2 - \psi_c^2(n)])^{1/2}$, and where $\beta_n = \lambda \mu_n / 4\pi$, $\psi$ is the angle of incidence of the X-rays, and $\mu_n$ is the linear absorption coefficient of the layer n.

These recursive equations are solved by setting $R_{N, N+1}$ equal to 0 with layer n=N corresponding to the substrate and carrying out the resulting recursive calculations, starting at the bottom of the thin film stack. With layer n=1 corresponding to the vacuum, the product ($|R_{1,2}|^2$) of $R_{1,2}$ with its complex conjugate gives the ratio of the reflected X-ray intensity to incident X-ray intensity.

The theoretical modeling of X-ray reflection based on the classical Fresnel equations, as well as complications from the width of interfaces and microscopic surface roughness, are discussed in greater detail in the following references, each of which is hereby incorporated by reference in its entirety: L. G. Parratt, Phys. Rev. 95, 359 (1954); C. A. Lucas et al., J. Appl. Phys. 63, 1936 (1988); M. Toney, S. Brennan, J. Appl. Phys. 66, 1861 (1989).

One approach to measuring the film thicknesses of patterned semiconductor wafers using XRR relies on the recognition that the measured X-ray reflection curve can be attributed primarily to the thicknesses of the layers rather than the structure of the pattern. The wavelength of the X-rays used in the XRR measurement is on the order of a few angstroms. Compared to the feature size of the patterned wafers, which is on the order of 10,000 angstroms, the wavelength is very small. Therefore interference effects from the structure of the pattern itself are not important. The most noticeable effect is that the reflected X-ray intensity may be generally reduced since the portion of the light that is incident onto the sides and bottoms of the recesses contributes less to the reflected signal. When the depth of the recesses is large compared to the thickness of the layers being measured, one sees only minor changes in the X-ray reflectivity curve beyond the reduction in overall intensity.

As used herein, "patterned wafer" or "patterned semiconductor wafer" means a semiconductor wafer whose surface bears an artificial pattern whose features are small in size relative to the spot size of the X-ray probe beam. As noted above, typically, the measurement spot size for the probe beam is one millimeter or larger, while the features of the pattern are on the order of one micron in size, and even the test sites on a patterned wafer have dimensions typically smaller than 100 microns. Thus, there is typically at least an order of magnitude separating the X-ray probe beam spot size and the size of even the test sites on the patterned wafer.

Because of the similarity in shape of the X-ray reflectance curves, analysis of the X-ray reflectivity curve for a patterned wafer can be greatly simplified through comparison with measurements made on an unpatterned wafer having similar layers. The unpatterned comparison wafer could be simply an unpatterned region on the patterned wafer, which unpatterned region underwent similar deposition as the patterned region.

In the case of the patterned wafer data, a simple transformation is applied based on the close resemblance of the patterned wafer reflectivity curve RP($\theta$) and the unpatterned wafer reflectivity curve RU($\theta$). (Here $\theta$ is the angle of incidence, but other dependent variables, such as the wave vector transfer, could also be used.) A transformation function T($\theta$) is chosen such that RP($\theta$)×T($\theta$) closely approximates RU($\theta$). The resemblance of RP($\theta$) and RU($\theta$) is such that T($\theta$) may appropriately be a simple linear function of $\theta$. However, more complex functions could also be chosen so that, for example, T($\theta$) could appropriately be a quadratic or cubic function of $\theta$ or a "splicing" of such functions for different portions of the angular spectrum.

Using a simple linear transformation function, T($\theta$), the data for the patterned wafer can be transformed. The same Fresnel equation modeling that are applied to an unpatterned wafer can be applied to the transformed reflectivity data to find the layer thicknesses for a patterned wafer. The necessary parameters can be found through an iterative nonlinear least squares optimization technique such as the well-known Marquardt-Levenberg. algorithm. A suitable iterative optimization technique for this purpose is described in "*Multi-parameter Measurements of Thin Films Using Beam-Profile Reflectivity*," Fanton et al., Journal of Applied, Physics, Vol. 73, No.11. p.7035 (1993) and "*Simultaneous Measurement of Six Layers in a Silicon on Insulator Film Stack Using Spectrophotometry and Beam Profile Reflectometry*," Leng et al., Journal of Applied Physics, Vol. 81, No. 8, p.3570 (1997). These two articles are hereby incorporated by reference in their entireties.

Once the layer thickness is determined, one can then analyze the full R-$\Psi$ curve and obtain values for density and surface and interface roughness.

Another approach to finding the layer thicknesses for an unpatterned wafer is to use a Fourier transform analysis. Fourier transform analysis was applied to find layer thicknesses of polymer systems in Seeck et al., Appl. Phys. Left. 76, 2713 (2000), hereby incorporated by reference in its entirety.

In another approach, when different fringe regimes are discernible in the data, the thicknesses of the metal films on a patterned wafer can be determined by reference to a modified Bragg equation as follows:

$$\sin^2\Psi_i = \sin^2\Psi_c + (i+½)^2(\lambda/2d)^2$$

where "$\Psi_i$" is the angle at which there is a fringe maximum, $\Psi_c$ is the critical angle, i is a positive integer with values 1, 2, 3, . . . , $\lambda$ is the X-ray wavelength, and d is the layer thickness.

Since $\Psi_i$ and $\Psi_c$ are very small angles, and since the modified Bragg equation must be valid for all critical angles, including $\Psi_c$=0, under this approximation the angular spacing between adjacent interference fringes is a constant for a given thickness d and is given by:

$$\Delta\Psi = \lambda/2d$$

Using this approach, a thickness $d(\Delta\Psi)=\lambda/(2\Delta\Psi)$ can be associated with each fringe spacing in the curve. Since the approximative Bragg equation becomes more valid as the angle of incidence increases, an asymptotic analysis can be applied to find the true thickness d by plotting the values for $d(\Delta\Psi)$ as a function of increasing $\theta$ and extrapolating the asymptote.

Figure 3:
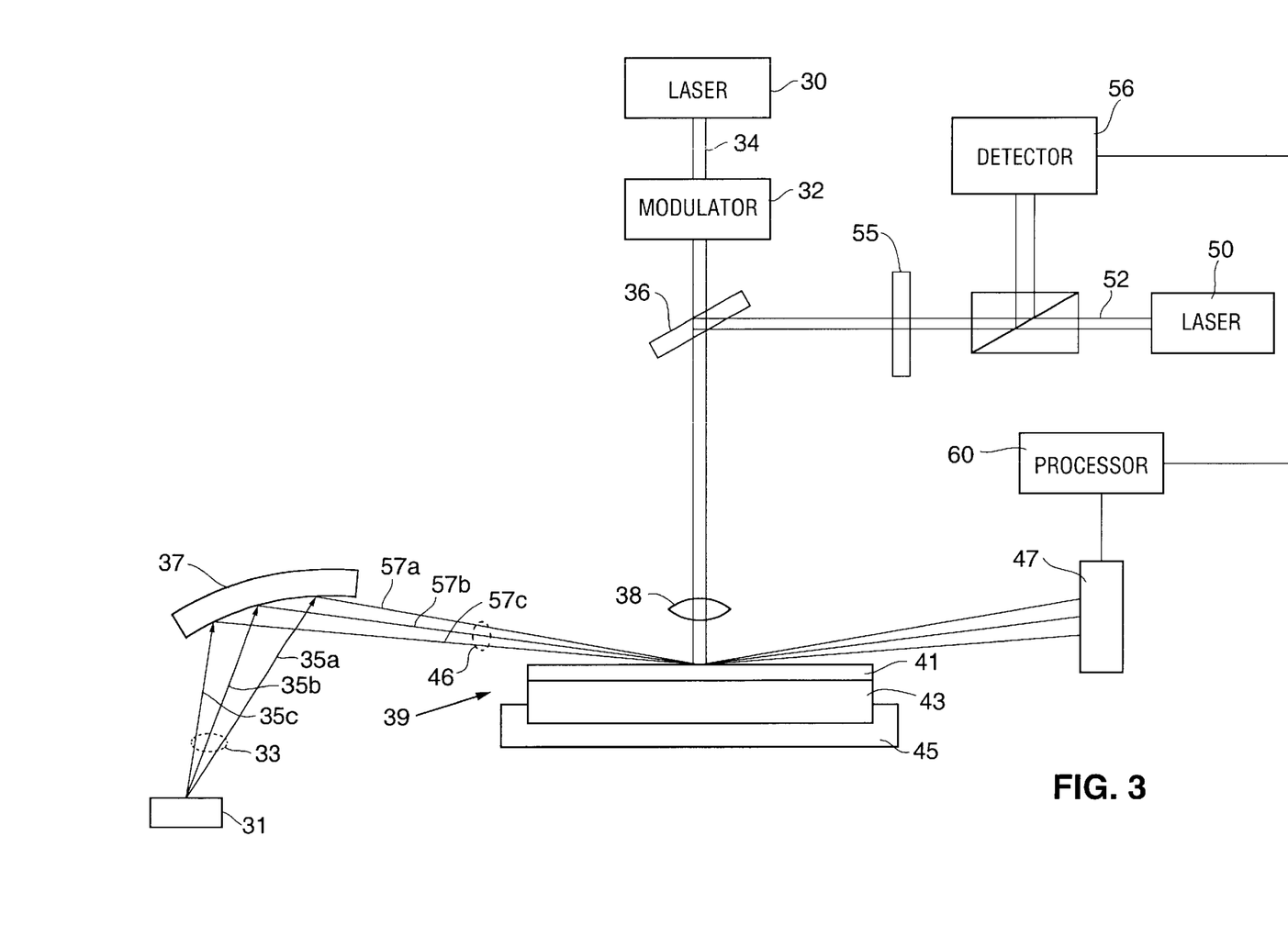
FIG. 3 is a composite block and schematic diagram of a unitary apparatus for carrying out both X-ray reflectometric measurements and thermal wave measurements in accordance with the subject invention

In the preferred embodiment, the two different measurement modalities represented by FIGS. 1 and 2 would be arranged so that the both measurements could easily be made in the same region of the sample. Typically, the measurements would be made sequentially. Given the geometries of the techniques, it would be possible to arrange the optical elements so that only a single stage is necessary. More particularly, and as shown in simplified form in FIG. 3, the pump and probe beams (34, 52) of the modulated optical reflectivity system can be directed normal to the sample surface. In contrast, the X-ray probe beam (bundle 46) is directed at near grazing incidence to the sample, thus permitting both optical systems to be arranged to measure essentially the same region on the sample. The data from both measurement modules can be supplied to a common processor 60 which can integrated with the same device or located remotely from the device. Using data taken by both modules from the same region on the sample will improve measurement accuracy.

The scope of the present invention is meant to be that set forth in the claims that follow and equivalents thereof, and is not limited to any of the specific embodiments described above.

What is claimed is:

1. A unitary apparatus for evaluating a sample comprising:
   (a) a first measurement module including:
      (i) means for inducing a periodic localized excitation at the surface of the sample;
      (ii) means for directing a first probe beam of radiation within a portion of the area periodically excited in a manner such that the first probe beam reflects from the surface of the sample;
      (iii) means for measuring the periodic variations of the reflected first probe beam induced by said periodic excitation to generate first output signals;
   (b) a second measurement module including:
      (i) means for generating a second probe beam, said second probe beam having X-ray wavelengths;
      (ii) means for directing said second probe beam onto the surface of said sample;
      (iii) a detector for measuring the intensity of X-rays reflected from said sample to generate second output signals; and
   (c) a processor for evaluating the sample based on a combination of the first and second output signals.

2. An apparatus as recited in claim 1 wherein said means for measuring the intensity of X-rays includes a photodiode detector.

3. An apparatus as recited in claim 1 wherein said first probe beam is generated by a laser.

4. An apparatus as recited in claim 1 wherein said means for measuring the first probe beam measures periodic changes in the magnitude or phase of the beam.

5. A method of evaluating a sample comprising the steps of:
   (a) obtaining a first set of measurements by:
      (i) inducing a periodic localized excitation on the surface of the sample;
      (ii) directing a first probe beam of radiation within a portion of the area periodically excited in a manner such that the first probe beam reflects from the surface of the sample; and
      (iii) measuring the intensity variations of the reflected first probe beam resulting from periodic changes of the sample induced by said periodic excitation to generate first output signals; and
   (b) obtaining a second set of measurements by:
      (i) generating a, second probe beam of X-rays;
      (ii) directing said second probe beam onto the surface of said sample;
      (iii) measuring the intensity of X-rays as reflected from said sample to generate second output signals; and
   (c) evaluating the sample based on a combination of the first and second output signals.

6. A method as recited in claim 5 wherein said step of evaluating the sample includes using either of the first or second output signals to characterize one parameter of the sample and wherein the other output signals are used to further characterize the sample with said one parameter being treated as a known parameter.

7. A method as recited in claim 5 wherein said step of evaluating the sample includes using the second output signal to characterize the density of a sample layer and wherein the first output signals are used to further characterize the sample with said layer density being treated as a known parameter.

8. A method as recited in claim 5 wherein said step of evaluating the sample includes using the second output signal to characterize the thickness of a sampler layer and wherein the first output signals are used to further characterize the sample with said layer thickness being treated as a known parameter.

9. A method as recited in claim 5 wherein said measuring of the intensity of X-rays includes using a photodiode detector.

10. A method as recited in claim 5 wherein said first probe beam of radiation is generated by a laser.

11. A method as recited in claim 5 wherein the periodic variations in the magnitude and/or phase of the first probe beam are measured.

12. A method of evaluating characteristics of a sample comprising the steps of:
   periodically exciting a region on the surface of the sample;
   monitoring the modulated optical reflectivity induced by said periodic excitation and generating first output signals in response thereto;
   directing a probe beam of X-ray radiation onto the same region on the sample surface;
   monitoring the non-modulated reflected power of the X-ray probe beam and generating second output signals in response thereto; and evaluating the characteristics of the sample based on a combination of the first and second output signals.

13. A method as recited in claim 12 wherein said step of evaluating the characteristics of the sample includes using either of the first or second output signals to characterize one parameter of the sample and wherein the other output signals are used to further characterize the sample with said one parameter being treated as a known parameter.

14. A unitary apparatus for evaluating characteristics of a sample comprising:

an intensity modulated excitation source for periodically exciting a region on the surface of the sample;

means for monitoring the modulated optical reflectivity induced by said periodic excitation and generating first output signals in response thereto;

means for obtaining X-ray reflectivity information from the same region on the sample surface and generating second output signals in response thereto; and a processor for evaluating the characteristics of the sample based on a combination of the first and second output signals.

15. An apparatus as recited in claim 14 wherein the processor uses either of the first or second output signals to characterize one parameter of the sample and wherein the other output signals are used to further characterize the sample with said one parameter being treated as a known parameter.

16. A unitary apparatus for evaluating characteristics of a sample comprising:

an intensity modulated pump beam directed to the sample for periodically exciting a region on the surface of the sample;

a first probe beam directed to reflect off the periodically excited region;

a first detection module having a photodetector for monitoring the modulated changes in the reflected first probe beam induced by said periodic excitation and generating first output signals in response thereto;

a second probe beam of X-rays directed to reflect off the same region on the sample surface;

a second detection module for monitoring the non-modulated reflected power of the second probe beam and generating second output signals in response thereto; and a processor for evaluating the characteristics of the sample based on a combination of the first and second output signals.

17. An apparatus as recited in claim 16 wherein the first detection module monitors the modulated variations in the magnitude and/or phase of the first probe beam.

18. An apparatus as recited in claim 16 wherein the processor uses either of the first or second output signals to characterize one parameter of the sample and wherein the other output signals are used to further characterize the sample with said one parameter being treated as a known parameter.

* * * * *